United States Patent [19]

Lynch

[11] 4,147,709
[45] Apr. 3, 1979

[54] ZIRCONIUM HALOHYDRIDE PREPARATION

[75] Inventor: Gary J. Lynch, St. Louis, Mo.

[73] Assignee: Monsanto Company, St. Louis, Mo.

[21] Appl. No.: 793,003

[22] Filed: May 2, 1977

[51] Int. Cl.² .............................................. C07F 7/00
[52] U.S. Cl. .................................................. 260/429.3
[58] Field of Search ....................... 260/429.3, 429 CY

[56] References Cited

PUBLICATIONS

Wailes et al., J. Organometal. Chem. 24 405–411 (1970); 28 91–95 (1971).
Hart et al., J.A.C.S. 96 8115–8116 (1974).
Eméleus, Adv. in Inorganic Chem. & Radiochem., Academic Press, N.Y. V7, pp. 116–118 (1965).
Candlin et al., Reactions of Transition–Metal Complexes, Elsevier Publ. Co., N.Y., pp. 328–330 (1968).

*Primary Examiner*—Helen M. S. Sneed
*Attorney, Agent, or Firm*—S. M. Tarter; E. P. Grattan; F. D. Shearin

[57] ABSTRACT

Zirconium halohydrides having the formula

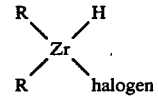

wherein R is a π-cyclopentadienyl radical are prepared by reacting a dihalide having the formula

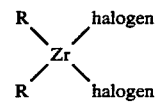

with molecular hydrogen in the presence of an unreacted Group Ia metal in a solvent for the dihalide.

10 Claims, No Drawings

ZIRCONIUM HALOHYDRIDE PREPARATION

BACKGROUND OF THE INVENTION

It has been recently discovered that zirconium chlorohydrides having the formula

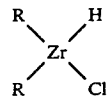

wherein R is an unsubstituted π-cyclopentadienyl radical are attractively useful in terminally functionalizing either internal or terminal olefins. In accordance with such utility, reaction of the chlorohydride with the olefin under mild conditions (e.g. 25°–40° C. in benzene) rapidly produces an alkylzirconium complex, the alkyl moiety of which is 1-substituted and the zirconium moiety of which can be readily replaced with a desired functional group, e.g. by cleaving the complex with an electrophilic reagent such as $Br_2$, $I_2$ or $C_6H_6ICl_2$ to prepare a terminally halogenated alkane or by first inserting a CO radical into the C—Zr bond of the complex and then cleaving the complex with a similar electrophilic reagent to prepare an alkane having a terminal acylhalide substituent. Illustrations of such uses of a di(π-cyclopentadienyl) zirconium chlorohydride have been published by J. Schwartz and other in J. Amer. Chem. Soc. at 96, 8115–16 (1974) and 97, 228–30 and 679–80 (1975) and in Angew. Chem. Int. Ed. Engl. at 15, No. 6, 333–40 (1976).

From those published illustrations it is apparent that the di(π-cyclopentadienyl) chlorozirconium moiety cleaved from the alkylzirconium complex by use of such an electrophilic group is concurrently further halogenated, producing a corresponding dihalide, and that one mole of the zirconium chlorohydride is converted to such a dihalide for each mole of olefin that is terminally functionalized. Thus the economic attractiveness of the olefin terminalizing process is highly dependent on the availability of a convenient procedure for converting the zirconium dihalide back to the chlorohydride which may be recycled for use in terminalizing more of the olefin.

Preparations of chlorohydrides of this kind from the corresponding dihalides have been previously described. For example, in J. Organometal. Chem., 24, 405–11 (1970), P. C. Wailes and H. Weigold describe the preparation of a di(π-cyclopentadienyl) zirconium chlorohydride by treatment of the corresponding dichloride with a stoichiometric amount of an alkali metal aluminum hydride which may be $LiAlH_4$ or $LiAlH$-(O-t-butyl)$_3$, and in J. Amer. Chem. Soc., 96, 8115–16 (1974), O. W. Hart and J. Schwartz describe carrying out the same reaction by treating the dihalide with Vitride, i.e. a solution of $NaAlH_2(OCH_2CH_2OCH_3)_2$ in benzene. A preparation of the same chlorohydride by treatment of the dichloride with metallic magnesium in tetrahydrofuran is also described in the aforementioned article by Wailes and Weigold. Each of those procedures, however, has serious drawbacks for commercial application. For instance, the alkali metal aluminum hydrides used as just mentioned are very expensive and, as described in the article by Wailes and Weigold, the yield of the procedure carried out with metallic magnesium is quite low (on the order of 30%).

Other attempts to convert such a dichloride to the corresponding chlorohydride have been completely unsuccessful. For instance, an uncatalyzed contacting of the same dichloride with molecular hydrogen under elevated pressure at 25° C. produced no discernible reaction, and the addition of a well-known homogeneous hydrogenation catalyst (tris-triphenylphosphine rhodium chloride) to the mixture likewise resulted in no detectable reaction.

It will be clear from the foregoing that a process by which the aforementioned and similar zirconium halohydrides can be more attractively produced from the corresponding dihalides is very desirable, and it is an object of this invention to provide such a process. Further objects of this invention will be apparent from the following disclosure in which all percentages are by weight except where otherwise noted.

SUMMARY OF THE INVENTION

This invention provides a process for preparing a zirconium halohydride having the structural formula

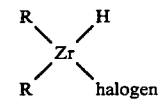

wherein each R is a π-cyclopentadienyl radical, which process comprises reacting a zirconium dihalide having the structural formula

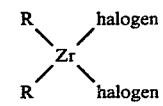

wherein each R has the aforedescribed significance with molecular hydrogen in the presence of an unreacted metal from Group Ia of the Periodic Table of the Elements in a solvent for the dihalide that does not prevent formation of said halohydride and at a temperature below that at which the halohydride decomposes.

DESCRIPTION OF THE PREFERRED EMBODIMENTS

The radicals represented by R in the foregoing dihalide formula may be the same as or different from each other and are, in general, any π-cyclopentadienyl radicals which are directly linked to the Zr atom in that formula and which do not prevent substantial formation of the desired halohydride reaction product. The dihalides containing such radicals are preferably liquid or soluble in the reaction system, and the halohydrides produced therefrom should be recoverable from that system. Typical but not limiting examples of such dihalides include those in which each R is a π-cyclopentadienyl radical that is unsubstituted (i.e., devoid of ring substituents other than hydrogen) or a substituted π-cyclopentadienyl radical such as a π-indenyl, π-fluorenyl, tetrahydro-π-indenyl, octahydro-π-fluorenyl, pentamethyl-π-cyclopentadienyl, pentaethyl-π-cyclopentadienyl, heptamethyl-π-indenyl, nonamethyl-π-fluorenyl or undecamethyl-tetrahydro-π-indenyl radical. Any of such radicals can be differently or further substituted (e.g. with other normal alkyl or cycloalkyl groups, with branched alkyl groups or with alkoxy or phenoxy groups) provided such substituents do not prevent substantial formation of the desired halohydride reaction product.

Certain of such substituents may advantageously increase solubility of the dihalide in a solvent employed in the process of this invention, and a considerable amount of such substitution may be present in some cases. When there is alkyl substitution of such radicals it is typical for each alkyl substituent to contain from 1 to about 12 and even more typically from 1 to about 4 carbon atoms and/or for the average number of carbon atoms per alkyl substituent to be not greater than about 2.

Other examples of substituents optionally present on a $\pi$-cyclopentadienyl ring in the radicals represented by R include various polymeric materials such as, for example, a polystyrene. In some embodiments, it may be advantageous for such a polymeric material to have sufficient molecular weight that it is a solid (e.g. a polymeric resin) under the conditions of the process of this invention, thereby facilitating maintenance of the halohydride in a fixed position for ease of product separation in an olefin-terminalizing process of the kind mentioned hereinbefore.

The halogen constituents of the zirconium dihalide employed in the process of this invention can be any of those in Group VIIa in the Periodic Table of the Elements. However, chlorine and bromine are generally preferred for economic reasons, and chlorine is normally most preferred.

Any of such ring-substituted zirconium dihalides can be prepared by procedures described in the art for making of the corresponding zirconium dihalide devoid of ring substituents other than hydrogen, and then alkylating or otherwise substituting the ring(s) thereof in accordance with other procedures known in the art for ring-substitution of similar carbocyclic compounds. Alternatively, by another procedure known in the art, such dihalides can be prepared by reacting a zirconium tetrahalide with an appropiate $\pi$-cyclopentadienyl sodium salt, which can be made by reacting sodium hydride with an alkyl-$\pi$-cyclopentadiene having the additional substituents desired on the dihalide to be used in the process of this invention.

Although this process may be carried out satisfactorily using a dihalide comprising $\pi$-indenyl or $\pi$-fluorenyl radicals, it is a preferred embodiment of the process which utilizes a dihalide comprising two mono-cyclic $\pi$-cyclopentadienyl radicals such as, for example, unsubstituted $\pi$-cyclopentadienyl or pentamethyl-$\pi$-cylocpentadienyl radicals.

As aforesaid, this process is carried out by reacting the dihalide with molecular hydrogen. Preferentially, the gaseous phase of the reaction mixture is essentially completely composed of molecular hydrogen, but there may also be present other gases (e.g. argon, helium and possibly nitrogen) which do not prevent substantial formation of the desired halohydride product or result in formation of intolerable amounts of undesirable by-products. Although the total pressure in the gaseous phase may range from below about 1 to above about 50 atmospheres, it is usually preferred that the partial pressure of molecular hydrogen therein is between about 1 and about 35 atmospheres and even more generally between about 1 and about 20 atmospheres. The importance of the use of molecular hydrogen in the present process is further apparent from a comparison of the results of this process and the disclosure by P.C. Wailes and H. Weigold in J. Organometal. Chem. 28, 91–95 (1971) that when such a dihalide was reduced with one equivalent of sodium amalgam or naphthalide under purified argon in an attempt to make the corresponding zirconium (III) monohalide, the product was polymeric.

Also as aforesaid, this process is carried out by reacting the dihalide with molecular hydrogen in the presence of an unreacted metal from Group Ia of the Periodic Table, i.e. an alkali metal such as Na, K, Li, Rb or Cs. Of those metallic elements, Na, K and Li are generally most desirably used and Na is especially preferred. The amount of alkali metal employed can be varied over a wide range, but as it reacts with the dihalide in stoichiometrically equivalent amounts it is typical practice to use a minor (less than 50%) and preferably small (e.g. 5–20%) stoichiometric excess of the alkali metal together with sufficient stirring or other agitation of the mixture to insure that the reducing power of the alkali metal is efficiently used.

Also as aforesaid, the present process is carried out in a solvent for the dihalide that does not prevent substantial formation of the desired halohydride product. Normally, there are various solvents which can be used satisfactorily. For example, ethereal solvents such as dioxane, tetrahydropyran, tetrahydrofuran, diethylether and ethylene glycol dimethyl ether (glyme) are generally superior solvents for such use, and tetrahydrofuran is especially preferred. Ethylether, dimethylether and anisole are other ethereal solvents which may be similarly used. Various tertiary amines (e.g. trimethylamine) and aromatic hydrocarbons (e.g. benzene, toluene, the xylenes and naphthalene) are similarly useful, and it may be advantageous in some cases to use such an aromatic hydrocabon (preferably benzene) as the reaction medium for both the process of this invention and the aforementioned procedure in which the resulting halohydride is used for terminalizing of an olefin, thereby avoiding the need for separation of solvent from the halohydride prior to its use in the olefin terminalizing procedure.

The process of this invention can be carried out at any convenient temperature below that at which the halohydride product decomposes. In general, that temperature is between about 0° and about 150° C., and even more typically between about 25° and about 140° C.

The following specific examples are illustrative only and do not imply any limitations on the scope of the invention.

EXAMPLE 1

To a well-stirred mixture of 0.91 grams of a 50% dispersion of 15–20 micron metallic sodium in paraffin and 5 ml of tetrahydrofuran (THF) under a molecular hydrogen atmosphere at 25° C. there is added a solution of 5.77 grams of di($\pi$-cyclopentadienyl) zirconium dichloride (MW=292.1) in 50 ml of THF, and the reaction mixture is immediately thereafter pressurized with 6.1 atm. of molecular hydrogen. After three hours the pressure has dropped to 2.36 atm., and the mixture is repressurized with hydrogen to 6.65 atm. After six additional hours the pressure has fallen to 5.64 atm. and then to 5.43 atm. after still another eight hours. The solids in the mixture are allowed to settle and the liquid is decanted. The solid is suspended in fresh THF and then centrifuged. The solid is then washed 5 times with THF and dried in vacuum, providing 4 grams of a dry red-brown powder. Assuming production of the theoretical quantity of by-product NaCl, the red-brown powder contains 71% ($\pi$-cyclopentadienyl)$_2$ZrClH which corresponds to a 55% reaction yield. An IR spectrum (mineral oil mull) of this powder is identical to that of ($\pi$-cyclopentadienyl)$_2$ZrClH (MW=257.6) prepared as described in the aforementioned J. Amer. Chem. Soc. 96, 8115–16 (1974) article by Hart and Schwartz.

Proof of the chemical activity of the hydride produced as described in this example for purposes of the olefin terminalizing procedure referred to hereinbefore is established by the hydrozirconation/bromonalysis procedure described in that same article by Hart and Schwartz. In accordance therewith, the hydride produced as described in this example is reacted with 1-dodecene in benzene. Bromonalysis of the resulting ($\pi$-cyclopentadienyl)$_2$-ZrCl(n-C$_{12}$H$_{25}$) shows a yield of n-C$_{12}$H$_{25}$Br which is essentially identical to the yield obtained using the ($\pi$-cyclopentadienyl)$_2$ZrClH prepared as described in the article by Hart and Schwartz.

EXAMPLES 2–4

When the procedure of Example 1 is essentially duplicated except that the ($\pi$-cyclopentadienyl)$_2$ZrCl$_2$ is replaced with an equimolar amount of (pentamethyl-$\pi$-cyclopentadienyl)$_2$ZrCl$_2$, ($\pi$-indenyl)$_2$ZrCl$_2$ or ($\pi$-fluorenyl)$_2$ZrCl$_2$, the results are similar. That is, a substantial reaction yield of the corresponding zirconium chlorohydride is produced in each case.

EXAMPLES 5–12

When the procedures of each of Examples 1–4 are essentially duplicated except that the metallic sodium is replaced with an equimolar amount of metallic potassium or the zirconium dichloride reactants are replaced with equimolar amounts of the analogous zirconium dibromides, substantial reaction yields of the corresponding zirconium chlorohydrides or bromohydrides are similarly produced in each case.

Each of the zirconium halohydrides prepared by the process of this invention is useful in terminally functionalizing an internal or terminal olfein when employed in an appropriate olefin terminalizing process of the kind mentioned hereinbefore.

I claim:

1. A process for preparing a zirconium halohydride having the structural formula

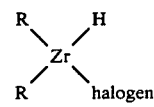

wherein each R is a $\pi$-cyclopentadienyl radical, which process comprises reacting a zirconium dihalide having the structural formula

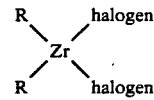

wherein each R has the aforedescribed significance with molecular hydrogen in the presence of an unreacted metal from Group Ia of the Periodic Table of the Elements in a solvent for the dihalide that does not prevent formation of said halohydride and at a temperature below that at which the halohydride decomposes.

2. The process of claim 1 wherein the unreacted metal is sodium or potassium.

3. The process of claim 1 carried out in an ethereal or aromatic hydrocarbon solvent for the dihalide.

4. The process of claim 1 wherein each R is an unsubstituted $\pi$-cyclopentadienyl or a pentamethyl-$\pi$-cyclopentadienyl radical.

5. The process of claim 1 wherein the halogen is chlorine.

6. The process of claim 5 wherein the unreacted metal is sodium or potassium.

7. The process of claim 5 carried out in an ethereal or aromatic hydrocarbon solvent for the dihalide.

8. The process of claim 5 wherein each R is an unsubstituted $\pi$-cyclopentadienyl radical.

9. The process of claim 8 wherein the unreacted metal is sodium, the temperature is between about 0° and about 150° C. and the solvent is selected from the group consisting of dioxane, tetrahydropyran, tetrahydrofuran, diethyl ether, ethylene glycol dimethyl ether, benzene, toluene and the xylenes.

10. The process of claim 9 carried out under a molecular hydrogen pressure between about 1 and about 35 atmospheres and wherein the solvent is tetrahydrofuran and the temperature is between about 25° and about 140° C.